United States Patent
Middelmann

(10) Patent No.: US 8,721,178 B2
(45) Date of Patent: May 13, 2014

(54) DENTAL PRODUCT FOR MAGNITUDE-CORRECT EVALUATION OF X-RAY IMAGES OF AREAS TO BE DIAGNOSED WITHIN THE ORAL CAVITY OF A PATIENT, AND USE OF A DENTAL PRODUCT

(76) Inventor: Heinrich Middelmann, Unterschleisshelm (DE)

( * ) Notice: Subject to any disclaimer, the term of this patent is extended or adjusted under 35 U.S.C. 154(b) by 464 days.

(21) Appl. No.: 13/055,549

(22) PCT Filed: Jul. 27, 2009

(86) PCT No.: PCT/EP2009/059661
§ 371 (c)(1),
(2), (4) Date: Jan. 24, 2011

(87) PCT Pub. No.: WO2010/012680
PCT Pub. Date: Feb. 4, 2010

(65) Prior Publication Data
US 2011/0123002 A1  May 26, 2011

(30) Foreign Application Priority Data
Jul. 30, 2008  (DE) .......................... 10 2008 035 504

(51) Int. Cl.
*A61B 6/14*  (2006.01)
(52) U.S. Cl.
USPC ........................................................ 378/204
(58) Field of Classification Search
USPC .................... 378/38, 62, 204, 207; 433/75
See application file for complete search history.

(56) References Cited

U.S. PATENT DOCUMENTS 5,573,400 A * 11/1996 Asher ........................... 433/136
5,878,104 A    3/1999 Ploetz
(Continued)

FOREIGN PATENT DOCUMENTS

DE     1022353      4/1955
KR  20050000934 A   1/2005

OTHER PUBLICATIONS

International Search Report for PCT/EP2009/059661 dated Nov. 2, 2009.
(Continued)

*Primary Examiner* — Irakli Kiknadze
(74) *Attorney, Agent, or Firm* — Pearne & Gordon LLP

(57) ABSTRACT

A dental product for the evaluation, according to scale, of X-ray recordings of areas which are to be diagnosed, in particular areas of the tooth and/or jawbone, within the oral cavity of a patient, has a main body 10', the shape of which is such that it is able to be received by the patient and is able to be fixed in the immediate vicinity of the area which is to be diagnosed by X-raying. The main body 10' consists of a material which is penetrable by X-ray beams, wherein in the interior of the main body at least one reference object 12' is held, which consists of material which absorbs X-ray beams. For the diagnosis, the dental product is placed into the patient's mouth and is fixed in that the patient bits onto the dental product. An image of the diagnosed area, which is initially distorted on X-raying, is calculated in a correcting manner by means of the known size of the at least one reference object held in the interior of a main body of the dental product, so that a display, according to scale, is possible.

9 Claims, 2 Drawing Sheets

(56) References Cited

U.S. PATENT DOCUMENTS

Figure 1:
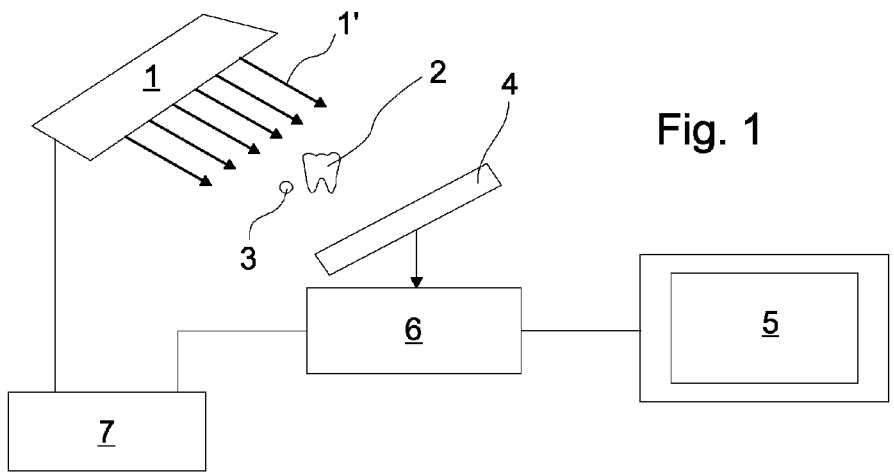

| | | | |
|---|---|---|---|
| 6,289,235 | B1 | 9/2001 | Webber et al. |
| 2006/0241406 | A1 | 10/2006 | Noujeim |
| 2006/0257817 | A1* | 11/2006 | Shelton ............................ 433/75 |
| 2006/0293581 | A1* | 12/2006 | Plewes et al. ................. 600/407 |
| 2008/0032257 | A1* | 2/2008 | Muckler .......................... 433/75 |

OTHER PUBLICATIONS

International Preliminary Report for PCT/EP2009/059661 dated Jul. 7, 2010.

* cited by examiner

DENTAL PRODUCT FOR MAGNITUDE-CORRECT EVALUATION OF X-RAY IMAGES OF AREAS TO BE DIAGNOSED WITHIN THE ORAL CAVITY OF A PATIENT, AND USE OF A DENTAL PRODUCT

The invention relates to a dental product for the evaluation, according to scale, of X-ray recordings of areas which are to be diagnosed, in particular areas of the tooth and jawbone, within the oral cavity of a patient.

Belonging to the background of the invention is the fact that in diagnostics in the dental field, when X-ray recordings are usually to be produced, it is very difficult to produce the recordings free of distortion. The reason for this is that a parallel alignment of the X-ray recording device, of the object which is to be recorded, such as a tooth or a partial area of the jaw, and of the recording medium is generally not possible. In addition, it is generally not possible to align the X-ray beams in a precisely parallel manner. If a reference body with known dimensions is arranged in the immediate vicinity of the object which is to be recorded and is pictured with it, a measurement can be obtained for the oblique position between the recording plane and the object. By evaluation means which draw upon a correction factor which corresponds to the measurement of the oblique position, a distortion-free image of the recorded object can be obtained from a distorted image of the recorded object. However, it has proved to be difficult in practice to arrange a reference object in a simple and secure manner in the vicinity of the area which is to be recorded.

From DE 196 19 924 A1 it is known to arrange a reference object by adhesion to the object under examination. However, it is disadvantageous here that the adhesion, for example of a ball on the object under examination, such as a tooth, makes an unnecessarily large amount of preparation effort necessary before carrying out the actual X-ray recording, and it can, however, not be completely ruled out that the subsequent removal of the ball from the tooth does not leave behind damage to the tooth. If, as is also disclosed in DE 196 19 924 A1, a cap with at least one reference object is placed over the object under examination, e.g. relating to a tooth, then this also involves a not inconsiderable expenditure in terms of time and cost.

A registry device for anatomical data can be seen from US 2006/0241406 A1. Shaped bodies which are impenetrable by X-ray beams are introduced in a shapeable material. The material is able to be introduced into the mouth of a patient.

Through U.S. Pat. No. 6,289,235 B1, a system for creating three-dimensional images by synthesis of tomographic recordings belongs to the prior art. The system comprises a biting block which is able to be introduced into the mouth of a patient and on which a reference element is fastened.

KR 10-2005-000934 A shows a reference device in the form of a biting block, into which metal balls are introduced at regular intervals.

According to U.S. Pat. No. 5,878,104 as a device a cap is provided, on which reference bodies are arranged which are impenetrable by X-ray beams, and which is able to be placed on an object under examination, e.g. a tooth.

It is also known to use individual templates produced in the laboratory, or special silicone impression compounds, into which the at least one reference object is embedded.

A considerable expenditure of time is also necessary here in order to prepare the recording for the at least one reference object before use in the patient, with the costs involved therewith being considerable. After use of the template which is produced for one particular patient, it can not be used again and must be disposed of.

It is therefore an object of the invention to provide an alternative dental product for the evaluation, according to scale, of X-ray recordings of areas which are to be diagnosed, in particular areas of the tooth and/or jawbone, within the oral cavity of a patient, which is simple and favourably priced.

In addition, a simple use of a dental product is to be provided.

The problem is solved for a dental product for the evaluation, according to scale, of X-ray recordings of areas which are to be diagnosed, in particular areas of the tooth and/or jawbone, within the oral cavity of a patient in that the product has: a main body, the shape of which is such that it is able to be received by the patient and is able to be fixed in the immediate vicinity of the area which is to be diagnosed by X-raying, consisting of a material which is penetrable by X-ray beams, wherein in the interior of the main body at least one reference object is held, which consists of material which absorbs X-ray beams. The shape of the main body here is spherical or elongated and has a substantially circular cross-section.

Provision is made that the material of the main body is flexible or soft. It was, however, discovered that a roll of cellulose or a roll of wadding, known in the field of dentistry, constitutes a source material for the main body which is simple to handle and is reasonably priced. The at least one reference body can then be included in a suitable stage of the production of the roll of cellulose or wadding.

No fundamental restrictions exist with regard to the choice of the at least one reference body. The only concern is that the at least one reference body consists of an inherently stable material which absorbs X-ray beams or respectively is impervious to X-ray beams. The at least one reference object can be a pin or a small tube or a ball-like, 3-axially symmetrical body, in particular a ball. In particular steel or titanium can be chosen as the material. When two reference objects prove to be necessary for the evaluation, according to scale, of the X-ray recording, preferably balls are chosen as reference objects which have a known diameter of e.g. 0.5 mm and hence have a suitable proportion to conventional cellulose or wadding rolls, which are preferably used for the formation of the main body.

In the case of very high standards for the evaluation, according to scale, of X-ray recordings, it can prove to be necessary that more than two reference objects are provided which form a spatial composite, with the composite connectors between the reference objects consisting of almost X-ray-penetrable material.

In the use of a dental product, it is taken into account that for the evaluation, according to scale, of X-ray recordings of areas which are to be diagnosed, in particular of areas of the tooth and/or jawbone, within the oral cavity of a patient, at least one dental product is placed into the patient's mouth and is able to be fixed in such a manner in the immediate vicinity of the area which is to be diagnosed, by the patient fixing the at least one dental product by biting and an image of the diagnosed area, which is initially distorted on X-raying, is calculated in a correcting manner by means of the known size of the at least one reference object of material which is impervious to X-ray beams or respectively absorbs X-ray beams, which is held in the interior of a main body of the dental product, so that an image according to scale or respectively a display according to scale is produced.

Figure 2:
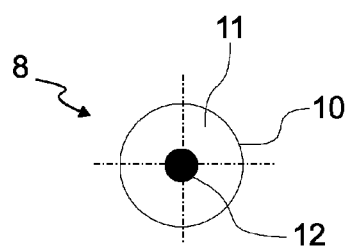
Figure 3:
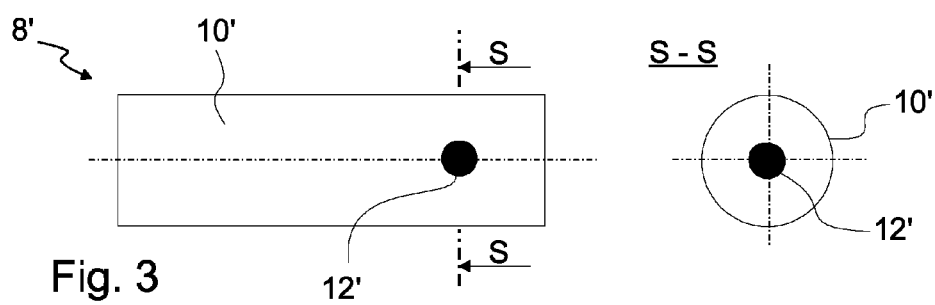
Figure 3:
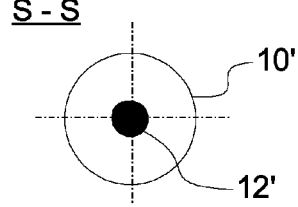
Figure 4:
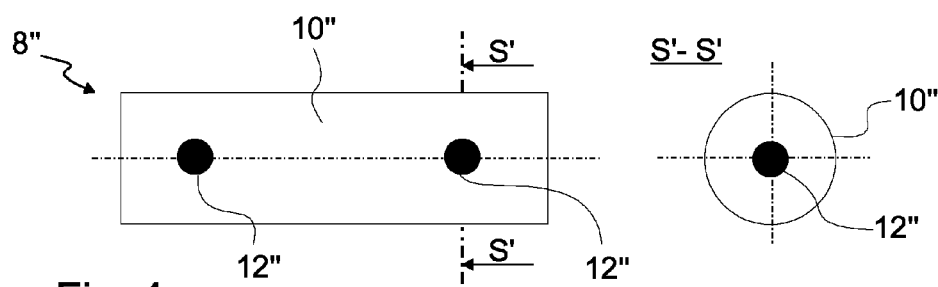
Figure 4:
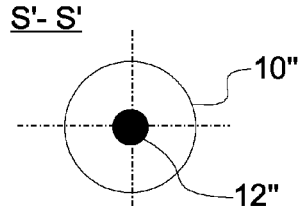
Figure 5:
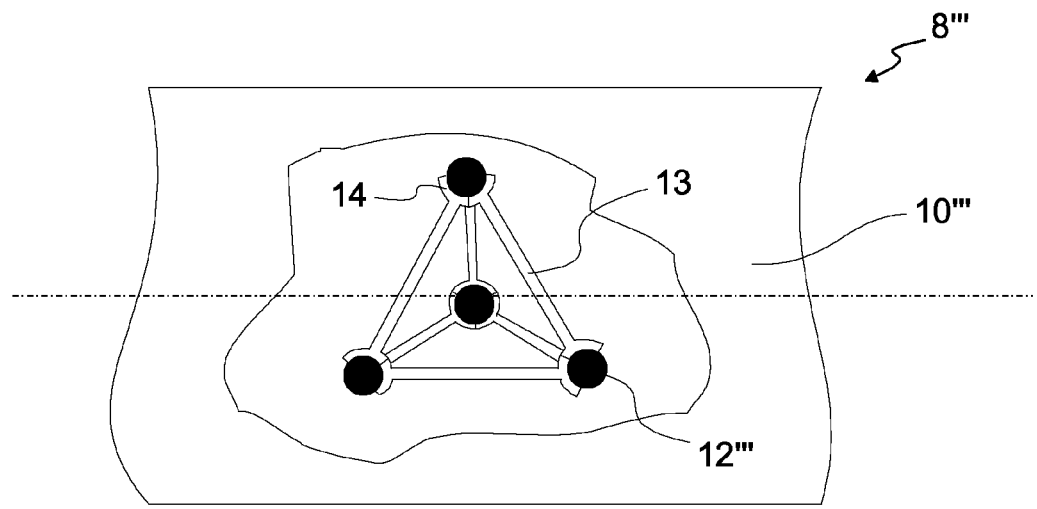
Figure 6:
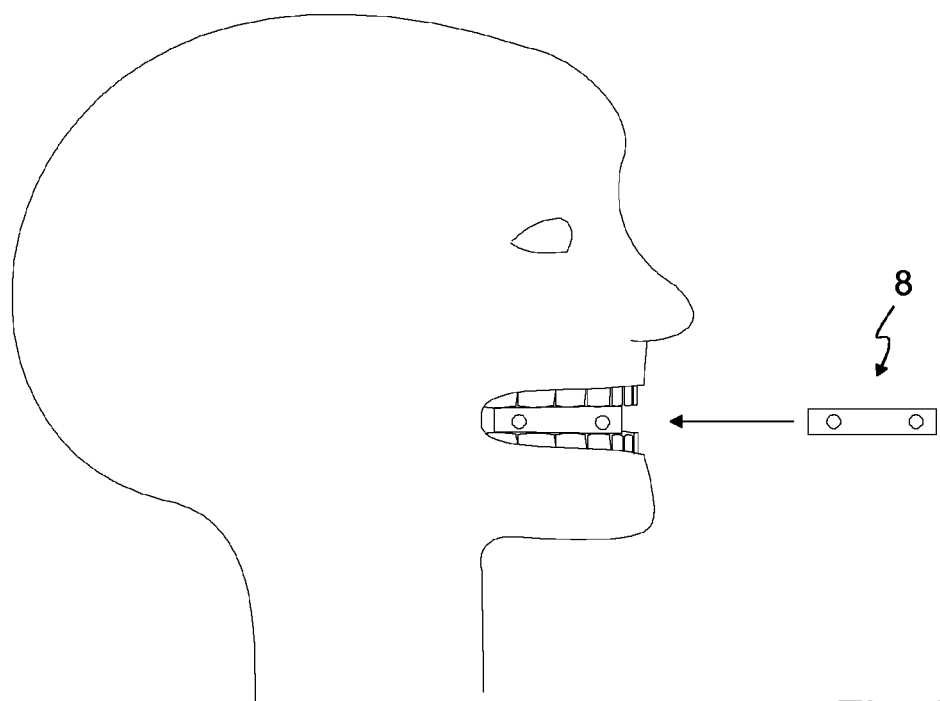

The invention is described below with the aid of example embodiments illustrated in the drawings with several figures, in which are shown:

FIG. 1 an X-ray diagnostics arrangement, as comes into use for example in the invention, FIG. 2 a somewhat larger illustration in section of the dental product according to the invention with a centrally held reference object, FIG. 3 an illustration, not to scale, of a side sectional view of the dental product according to the invention with a held reference object and alongside with illustrated cross-sectional view along section line S-S, FIG. 4 an illustration, not to scale, of a lateral sectional view of the dental product according to the invention with two held reference objects and alongside with illustrated cross-sectional view along section line S'-S', FIG. 5 a three-dimensional composite with more than two reference objects, introduced into the diagrammatically illustrated main body, and FIG. 6 a conventional introduction of the dental product according to the invention in the oral cavity of the patient and its fixing by biting An X-ray diagnostics arrangement coming into use for example in connection with the invention, but not belonging to the invention, is illustrated in FIG. 1. Originating from an X-ray radiation source 1, emerging X-ray beams 1' are directed to an area which is to be diagnosed with for example an object 2 which is to be examined, such as a tooth, in order to obtain an image on a recording medium 4. In addition to the object which is to be examined, a general reference object 3 of known dimension, made of inherently stable material which absorbs X-ray beams, such as e.g. a steel or titanium ball, is also pictured on the recording medium 4. The image of the object 2 to be examined, which is obtained on the recording medium 4, generally has a distortion. By means of the image of the reference object 3, which is also distorted, the original dimension of which is known—in the imaging of a ball, an ellipse is displayed instead of a circle—from the ratio of the semi-axes of the ellipse a measurement can be obtained for the oblique position of recording plane to imaging plane of the recording medium so that in addition with the known dimension of the reference object 3, by means of an evaluation unit 6, such as a computer, which is connected with the recording medium 4, e.g. in the highest version with a semiconductor array, a distortion-free representation of the object 2 under examination, such as a tooth, or a precise image of a bone structure in the periphery of a tooth, are obtained from the digital image of the object 2 under examination and reference object 3 accordingly from parameters entered through an operating panel 7 on a screen 5, which is connected with the evaluation unit 6. Suitable calculation algorithms come to be used in the evaluation unit 6, which with regard to their approach are all based on ratio calculations, also often designated as rule of three. In this way, the dimension of the bone structure can be calculated, which is a necessary prerequisite for the introduction for example of an implant.

A cross-section of the dental product 8 according to the invention is illustrated somewhat larger by FIG. 2. As the dental product 8 can also be a ball, this illustration is also appropriate for this. It can be seen how in a main body 10 with an interior 11 at least one reference object is held almost centrally. It is comfortable for the patient if the main body is flexible or soft. Cellulose or wadding is extremely suitable for this. However, other materials can also be used which have this—flexible/soft—characteristic. As the patient is to fix the main body by biting throughout the duration of the diagnostic process by X-ray, the extent of flexibility is to be taken into consideration in a suitable manner, because the reference object is not to be damaged or biting is not to cause pain to the patient. The concern is merely that the reference object is fixed in the region of the site of the bone which is to be examined or respectively measured during the recording. In addition, it is necessary for the material of the main body to be penetrable by X-ray beams.

A side view of the dental product according to the invention is illustrated by FIG. 3. The main body 10' has an elongated shape and a substantially circular cross-section. Surprisingly, it was able to be discovered that a cellulose roll or wadding roll, known in the field of dentistry, presents itself as excellently suitable for the main body. The at least one reference object can then be included in a suitable stage of the production of the cellulose or wadding roll.

According to FIG. 3, a reference object 12' is held in the main body 10' substantially in the region of its longitudinal axis but not centrally to its longitudinal dimension. Hereby, a subsequent use of the dental product is to be provided for with regard to better relatability of the reference object 12' to the area which is to be diagnosed.

An illustration was carried out by FIG. 4 of the dental product according to the invention with main body 10" and two held reference objects 12". By the two reference objects 12" on the one hand also a better relatability can be undertaken of one of the reference objects 12" to the area which is to be diagnosed by X-raying. On the other hand, it is possible, by two reference objects 12", to obtain more reference data, so that the evaluation arrangement 6 is able to carry out a still further improved evaluation, according to scale, and is able to display this on the screen 5.

In the main body 10' and 10" which can be seen according to FIGS. 3 and 4, the latter has an elongated shape. In a preferred embodiment of the invention, it can by formed by a cellulose or wadding roll. Firstly, no restricting requirements exist for the reference objects 12' and 12". A pin or a small tube or a ball can be chosen respectively as reference object. In particular, steel or titanium have proved suitable as material, because thereby the dimensional stability and capability of absorbing X-ray beams are particularly favourable. If a ball is chosen as reference object, it has proved to be advantageous to select its diameter at 0.5 mm.

A three-dimensional composite with more than two reference objects 12''', which are introduced into the diagrammatically illustrated main body 10''', is illustrated in FIG. 5. By more than two reference objects 12''' being available in the three-dimensional composite, further data can be obtained concerning the position and alignment to the object 2 under examination, which data are made available to the evaluation unit 6 from the recording medium 4, so that on the screen 5 by individual selection via the operating panel 7 more detailed images of the object under examination, according to scale to a greater extent, e.g. in several planes, can be displayed or brought for further storage. The connecting bridges 13 between the reference objects 12''' can consist of material almost penetrable by X-ray beams and can be formed for example from plastic. To receive the reference objects, the connecting bridges have extensions 14 which can hold the reference objects in a suitable manner.

A conventional introduction of the dental product according to the invention into the oral cavity of the patient and its fixing by biting is illustrated by FIG. 6. The dental product 8 is introduced into the oral cavity of the patient and is fixed by the patient by biting. The recording medium 4 can, as illustrated above, be a semiconductor array. However, a conventional X-ray film also comes into consideration as recording medium 4, which is placed into the patient's mouth together with the dental product 8. It is then necessary for the X-ray film to be read respectively, e.g. via a camera, and the digital image which is then obtained from the object under examination and from least one reference object 12 is supplied to an evaluation unit, corresponding to the above evaluation unit 6, in connection with an operating panel 7, in order to respectively display the individual recording, present on the X-ray film, on a screen, corresponding to the above screen 5, in an evaluated manner according to scale.

LIST OF REFERENCE NUMBERS

1 X-ray radiation source
1' X-ray beams
2 object under examination
3 reference object, general
4 recording medium
5 screen
6 evaluation unit
7 operating panel
8 dental product
10 main body (10', 10", 10''')
11 interior
12 reference object (of invention, 12', 12", 12''')
13 connecting bridges
14 extensions

The invention claimed is:

1. Dental product (8) for the evaluation, according to scale, of X-ray recordings of areas (2) which are to be diagnosed, in particular areas of the tooth and/or jawbone, within the oral cavity of a patient, having a main body (10), the shape of which is such that it is able to be received by the patient and is able to be fixed in the immediate vicinity of the area (2) which is to be diagnosed by X-raying, consisting of a material which is penetrable by X-ray beams, wherein at least one reference object (12) consists of material which absorbs X-ray beams, wherein the reference object (12) is held in the interior of the main body (10) and the main body (10) is spherical or has an elongated shape with a substantially circular cross-section, wherein the material of the main body (10) is flexible or soft, and wherein the main body (10) is formed by a cellulose or wadding roll.

2. Dental product according to claim 1, wherein the at least one reference object (12) is a pin or a small tube or a ball.

3. Dental product according to claim 2, wherein the material of the at least one reference object (12) is steel or titanium.

4. Dental product according to claim 1, wherein a ball is provided as reference object (12, 12').

5. Dental product according to claim 4, wherein the diameter of a ball is 0.5 mm.

6. Dental product according to claim 1, wherein two balls are provided as reference objects (12").

7. Dental product according to claim 6, wherein the diameter of a ball is 0.5 mm.

8. Dental product according to claim 1, wherein more than two reference objects (12''') are provided, which form a three-dimensional composite, wherein the connecting bridges (13) between the reference objects consist of material which is almost penetrable by X-ray beams.

9. Use of a dental product, in particular according to one of claims 1, and 2-8, wherein for the evaluation, according to scale, of X-ray recordings of areas which are to be diagnosed, in particular of areas of the tooth and/or jawbone, within the oral cavity of a patient, at least one dental product (8) is placed into the patient's mouth and is able to be fixed in such a manner in the immediate vicinity of the area which is to be diagnosed, by the patient fixing the at least one dental product by biting, and an image of the area which is to be diagnosed, which is initially distorted on X-raying, is calculated in a correcting manner by means of the known size of the at least one reference object of material absorbing X-ray beams held in the interior of a main body of the dental product, so that an image according to scale, or a display according to scale is produced, or respectively the dimensions of the bone structure in the diagnosis area is able to be calculated using the reference object.

* * * * *